United States Patent

Jau

(10) Patent No.: US 7,624,625 B2
(45) Date of Patent: Dec. 1, 2009

(54) MEASUREMENTS OF YIELD STRESS AND PLASTIC VISCOSITY OF CEMENT-BASED MATERIALS VIA CONCRETE RHEOMETER

(76) Inventor: Wen-Chen Jau, 2F., No. 8, Lane 86, Jiangong 1st Rd., East District, Hsinchu City (TW)

( * ) Notice: Subject to any disclaimer, the term of this patent is extended or adjusted under 35 U.S.C. 154(b) by 0 days.

(21) Appl. No.: 11/790,880

(22) Filed: Apr. 27, 2007

(65) Prior Publication Data

US 2008/0060423 A1    Mar. 13, 2008

(30) Foreign Application Priority Data

Apr. 29, 2006 (CN) .................. 2006 1 0079099

(51) Int. Cl.
*G01N 11/14* (2006.01)
(52) U.S. Cl. .................................... 73/54.31
(58) Field of Classification Search ............ 73/54.31, 73/54.28, 54.23, 54.01
See application file for complete search history.

(56) References Cited

U.S. PATENT DOCUMENTS

| | | | | |
|---|---|---|---|---|
| 4,594,883 A | * | 6/1986 | Pollard | 73/54.23 |
| 4,875,362 A | * | 10/1989 | Skallen | 73/54.31 |
| 5,321,974 A | * | 6/1994 | Hemmings et al. | 73/54.31 |
| 6,065,330 A | * | 5/2000 | Freeman et al. | 73/54.28 |
| 7,021,123 B2 | * | 4/2006 | Wallevik et al. | 73/54.02 |

* cited by examiner

*Primary Examiner*—Hezron Williams
*Assistant Examiner*—Gunnar J Gissel

(57) ABSTRACT

A rheometer can be used to measure yield stress and viscosity of a cement-based material with excellent results. It mainly includes a drum and at least one adaptive vane assembly. The adaptive vane assembly is replaceably connected to a shaft. The shaft rotates relative to the drum. The ratio of radius ($r_1$) of the adaptive vane assembly to radius ($r_o$) of the drum is between 0.1~0.6. The shaft is rotated with a minimum rotational speed more than 0.001 rad/s, and then can measure its torque at constant speed. Accordingly, the rheometer can greatly reduce the disturbance of vanes of the adaptive vane assembly upon the cement-based materials and reduce the slippage among particles and the vanes. Moreover, the minimum shear stress is defined as a yield stress.

10 Claims, 21 Drawing Sheets

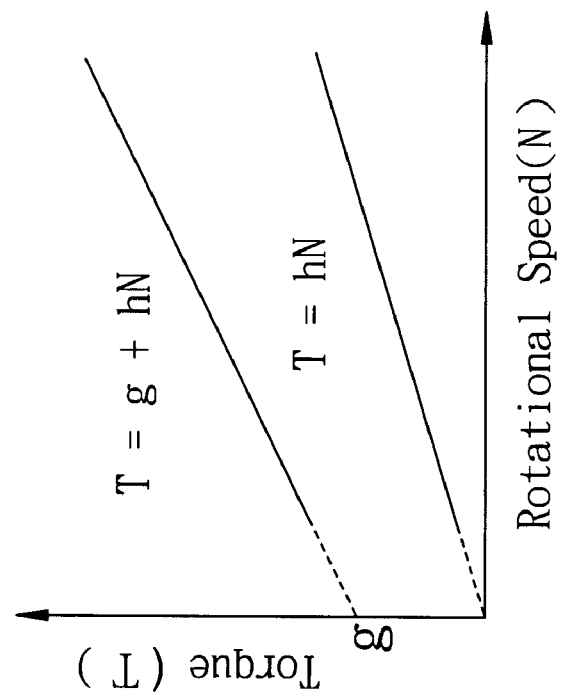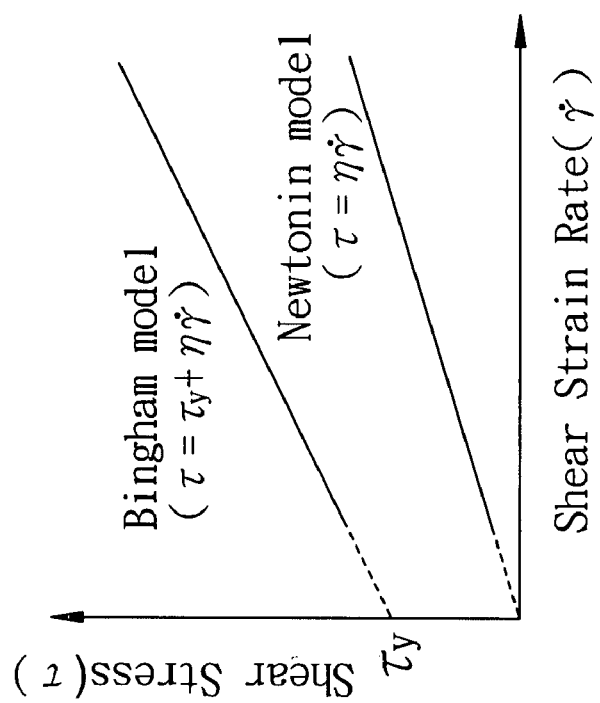
FIG. 2

1. The evaluation target of Powder-SCC:

| The rank of self-compactability | | 1 | 2 | 3 |
|---|---|---|---|---|
| structure condition | The min. spacing of the reinforcement (mm) | 35~60 | 60~200 | above 200 |
| | The amount of rebar (kg/m3) | above 350 | 100~350 | below 100 |
| The filling heigh of U box or box-shaped test (mm) | | above 300 (obstacles R1) | above 300 (obstacles R2) | above 300 (no obstacles) |
| Workability | Slump flow (mm) | 600~700 | 600~700 | 500~650 |
| Resistance to segregation | The flow time of $V_{75}$ funnel[1] (sec) | 9~20 | 7~13 | 4~11 |
| | Time to 500mm flow (sec) | 5~20 | 3~15 | 3~15 |

2. The evaluation target of VMA(2)-type SCC:

| The rank of self-compactability | | | 1 | 2 | 3 |
|---|---|---|---|---|---|
| structure condition | The min. spacing of the reinforcement (mm) | | 30~60 | 60~200 | above 200 |
| | The amount of rebar (kg/m3) | | above 350 | 100~350 | below 100 |
| The filling heigh of U box or box-shaped test (mm) | | | above 300 (obstacles R1) | above 300 (obstacles R2) | above 300 (no obstacles) |
| Workability | Slump flow (mm) | | 550~700 | | 500~650 |
| Resistance to segregation | flow time (sec) | $V_{75}$ funnel | 10~20 | 7~20 | 7~20 |
| | | $S_{100}$ funnel[3] | 4~8 | 3~8 | 3~8 |
| | Time to 500mm flow (sec) | | 5~25 | 3~15 | 3~15 |

3. The evaluation target of Combination-type SCC:

| The rank of self-compactability | | 1 | 2 | 3 |
|---|---|---|---|---|
| structure condition | The min. spacing of the reinforcement (mm) | 35~60 | 60~200 | above 200 |
| | The amount of rebar (kg/m3) | above 350 | 100~350 | below 100 |
| The filling heigh of U box or box-shaped test (mm) | | above 300 (obstacles R1) | above 300 (obstacles R2) | above 300 (no obstacles) |
| Workability | Slump flow (mm) | 650~750 | 600~700 | 500~650 |
| Resistance to segregation | The flow time of $V_{75}$ funnel[1] (sec) | 10~20 | 7~20 | 7~20 |
| | Time to 500mm flow (sec) | 5~20 | 3~15 | 3~15 |

Note (1): V75 funnel refers to a V-funnel with a cross section of discharge port sized in 75mm × 75mm.

(2) VMA = Viscosity-modifying admixture (3): $S_{100}$ funnel refers to a hollow cylindrical funnel made of steel. The straight pipe has an adjustable upper flange, a smooth inner wall of 98mm-diameter and 800mm-height, with a capacity of 6.28L, an opening at both ends, a discharge port at bottom fitted with a fast-switching, water-tight valve.

FIG. 23

MEASUREMENTS OF YIELD STRESS AND PLASTIC VISCOSITY OF CEMENT-BASED MATERIALS VIA CONCRETE RHEOMETER

FIELD OF THE INVENTION

The present invention relates generally to a new generation of rheometer, and more particularly to an improved one which is suitable to measure the rheology of cement-based materials (e.g. concrete, mortar, cement paste).

BACKGROUND OF THE INVENTION

To measure the rheology of various liquids, rheometers were designed in many different types, of which a typical rheometer can measure both the rheology of cement-based materials (e.g. concrete), and also the viscosity ($\eta$) and yield stress ($\tau_y$), as illustrated in two-point test in FIG. 1. The rheometer 100 includes a drum 110 to accommodate concrete, and a rotation shaft 120 driven by a motor 130 and connected to a plurality of vanes 121. This theory was initiated by G H Tattersall, and the rheology of concrete is simulated as Bingham fluid, for which a shear stress similar to static friction would exist prior to the initiation of shear strain. Only when the shear stress reaches a specific value, the shear strain rate ($\dot{\gamma}$) starts to change. The linear relationship between shear stress ($\tau$) and shear strain rate is shown in Eq. (1). By using two-point test apparatus, the relationship between measured torque (T) and rotational speed (N) can be converted into shear stress and shear strain rate shown in FIG. 2. The relationship is shown in Eq. (2).

$$\tau = \tau_y + \eta \dot{\gamma} \quad (1)$$

$$T = g + hN \quad (2)$$

Two indicators, the slope (h) and the intercept (g) of the T-N curve are used to determine the workability of concrete. The relationship among g, h and G, K are shown in Eqs. (3) and (4).

$$\tau_y = \frac{K}{G} g \quad (3)$$

$$\eta = \frac{1}{G} \times h \quad (4)$$

whereby G and K are the rheological constants of the vane. However, the vane 121 of rheometer 100 cannot be replaceably adjusted. And, the theory of rheological constant K shows that, an optimal spacing (minimum error) is achieved when the ratio ($r_1/r_0$) of radius ($r_1$) of vane to radius ($r_0$) of drum is more than 0.97. But, this spacing is suitable only for fluids not containing solid particles of certain sizes, such as coarse aggregates in concrete. When applied to concrete, vane 121 may be jammed if theoretical value of ratio ($r_1/r_0$) is set as 0.97. Thus, the ratio ($r_1/r_0$) of the radius of vane 121 to the radius of drum 110 is between 0.6~0.85, to avoid jams. Besides, a negative yield stress for self-consolidating concrete (SCC) has been found by using this technique. This is because SCC has a lower yield stress and the calculation of the regression line affects the intercept of the torque axis in such a way that it sometimes gives a negative value. The negative values are attributed to the error in the extrapolation process and have no real physical meaning. Further research is needed to develop a new technique to determine the yield stress of SCC.

SUMMARY OF THE INVENTION

One major purpose of the present invention is to provide a new generation of rheometer, which enables at least an adaptive vane assembly to be replaceably connected to a rotation shaft. The adaptive vane assembly contain as a minimum of two vanes suitable to measure the rheology of a cement-based material.

Another purpose of the present invention is to provide a rheometer (concrete rheometer). It is feasible to measure the plastic viscosity and yield stress of cement-based materials by the concrete rheometer, and compare with slump flow test, V-funnel times, J-Ring test and U-box test. The main source of error for two point test apparatus as mentioned by previous researches comes from segregation caused by disturbance and the gap width. A gap width smaller than the maximum aggregate size may cause the aggregates stuck between vane and the inner wall of the cylindrical vessel. Therefore, the invention uses larger diameter and a high-capacity cylindrical vessel to avoid the disturbance and the small gap problem such that the ratio of $r_1/r_0$ is between 0.1~0.6. The gap width ($r_0 - r_1$) is at least 2.5 times of maximum aggregate size which prevents the aggregates from being stuck and to avoid the friction from wall of cylinder which may cause an error to the measured torque. The rotational speed of rotation shaft is preferably set over 0.001 rad/s. In such case, it is more feasible to measure the torque, and reduce greatly the disturbance of concrete, thus making rheometer become an accurate rheology testing instrument.

The design of the concrete rheometer measurement system for this invention is shown in FIG. 3. Torque (T) and rotational speed (N) are measured and stored in the data acquisition system which is connected to a computer. The rotational speed can be controlled by a computer program or manually. The system can be programmed as constant speed, linear acceleration, quadratic acceleration, and progressive speed change. At least one adaptive vane assembly is connected to rotation shaft, such that it is possible to adjust properly according to cement-based materials of different mixture ratio. The adaptive vane assembly can be assembled into: 1, a vertical vane assembly (containing over 2 vanes, e.g.: 3 or 6 vanes); 2, one or more layers of vane assembly, each layer with over 2 vanes at any slope angle. At each layer, the included angle with horizontal plane (X-Y plane) to rotate clockwise or counter-clockwise. The vane of each layer can be adjusted to form a 3-D geometry.

The rheometer of the present invention could measure yield stress and viscosity of cementitious materials in the following methods: viscosity ($\eta$ unit: Pa·s)

The viscosity is computed using Eq. (5).

$$\eta = \frac{\dot{T}}{G} = \frac{dT}{dN} \times \frac{1}{G} \quad \left(Pa.s; \frac{N - \sec}{m^2}\right) \quad (5)$$

the unit of viscosity as poise $$\left(\frac{dynes - \sec}{cm^2}\right),$$

and 1 Pa·s equal 10 poise.

The plastic viscosity was obtained as fallows. The rotational speed was set from 0 rpm to expected rotational speed. The plastic viscosity was calculated by the product of the slope and G value as shown in Table 1 while the slope was obtained by the regression from torque vs. rotational speed.

Yield stress ($\tau_y$)

In this invention, the torque was measured at a rather low rotational speed (above 0.001 rad/s). Under the same rotational speed, the maximum torque ($T_{max}$) was transformed into the maximum shear stress ($\tau_{max}$) of concrete as shown in FIG. 4.

The maximum shear stress can be obtained by measuring the maximum peak value of torque under different low rotational speed as shown in FIG. 5, and multiplying the parameters of specific vanes ($\beta$) as shown in Table 1. Meanwhile, the minimum $\tau_{max}$ measured from the same sample is defined as yield stress ($\tau_y$).

The yield stress can be obtained by Eq. (6):

$$T = 2\pi \alpha R^2 H \tau_y + 4\pi \int_0^R \tau r^2 dr = 2\pi R^3 \tau_y (\alpha H/R + 2/3) \quad (6)$$

To simplify the calculation, it is assumed that the shear stress at upper and lower sides of the vane is $\tau_y$, so the original equation can be modified as follows:

$T = 2\pi R^3 \tau_y (\alpha H/R + \tfrac{2}{3})$ and $\tau_y = T/[2\pi R^3 (\alpha H/R + \tfrac{2}{3})] = T \times \beta$ (7)

α: percentage of vertical area
β: transform factor
α and β of three vanes are listed in Table 1.
T: torque (kgf-m)
R: vane radius
H: vane height
τ: shear stress (Pa) at upper and lower sides of the vane

DESCRIPTION OF THE DRAWINGS

FIG. 2 shows a transform of Bingham model.

FIG. 23 shows the proposed requirement for SCC depending upon different mixture and design method.

DETAIL DESCRIPTION OF THE INVENTION

Embodiment 1

Figure 1:
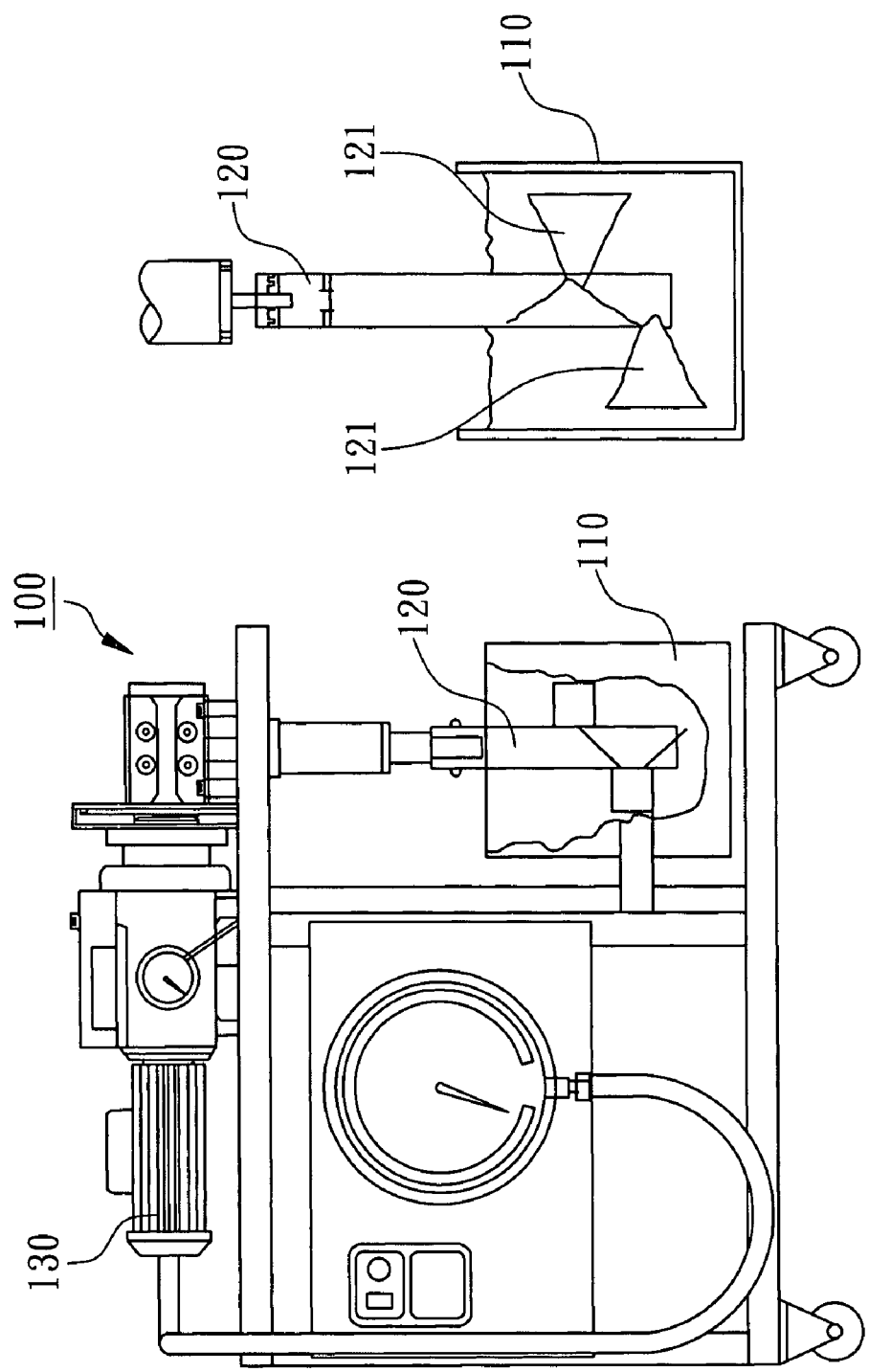
FIG. 1 shows a two-point test apparatus.
Figure 3:
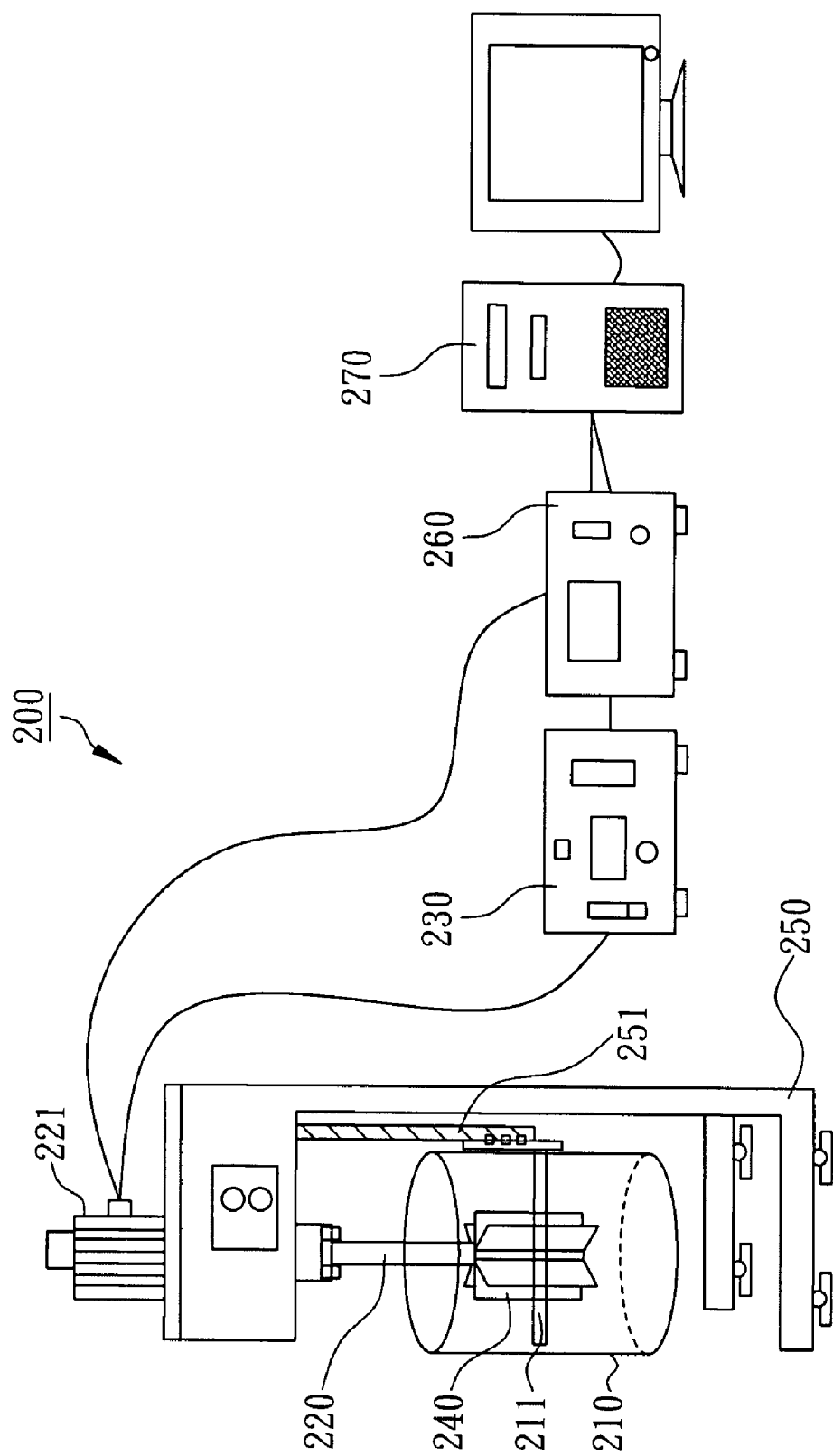
FIG. 3 shows a concrete rheometer measurement system schematic and dimensions.
Figure 4:
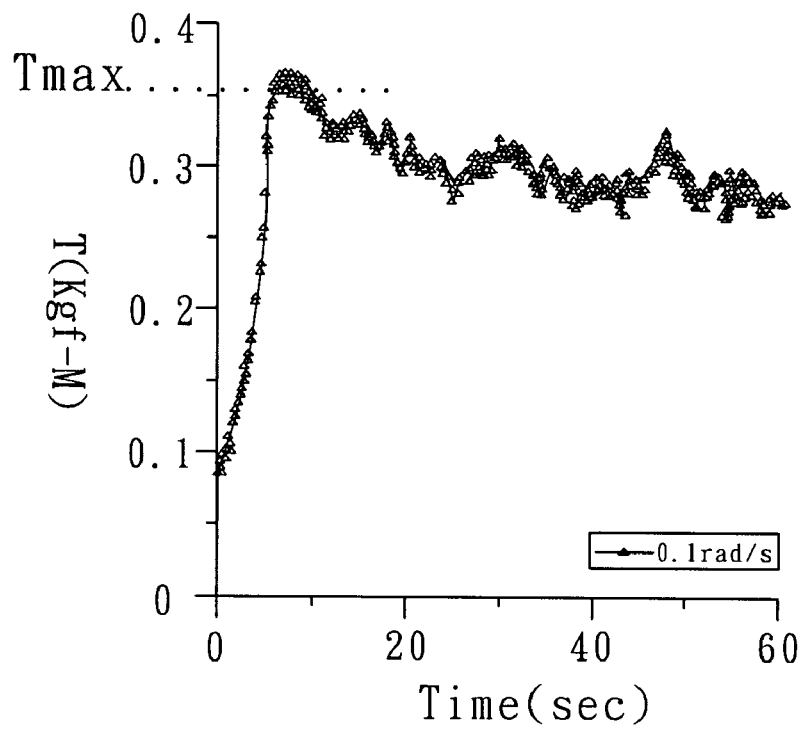
FIG. 4 shows a measurement method of maximum torque (e.g. HFC).
Figure 5:
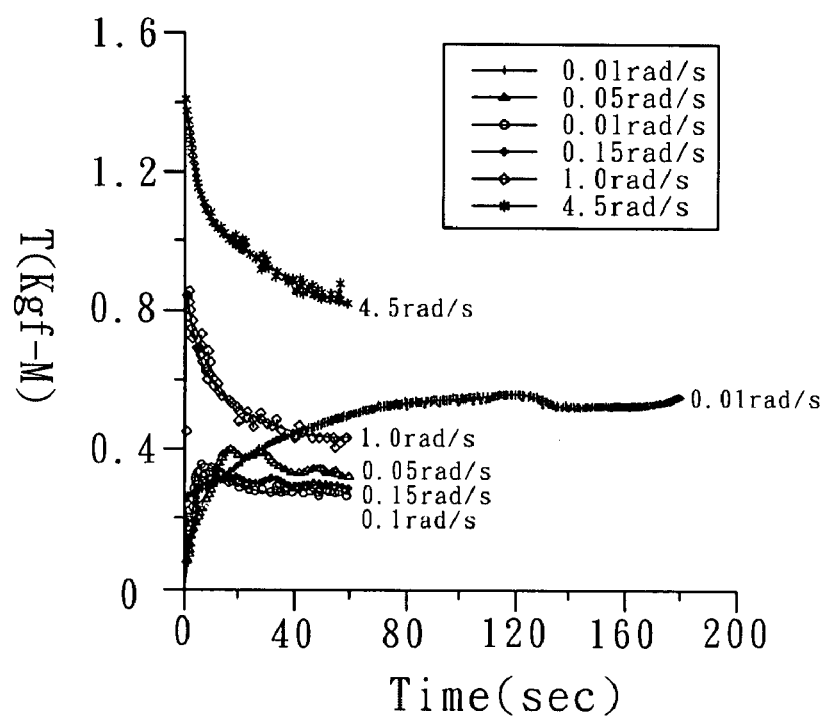
FIG. 5 shows a maximum shear stress under different rotational speeds (e.g. HFC).
Figure 6:
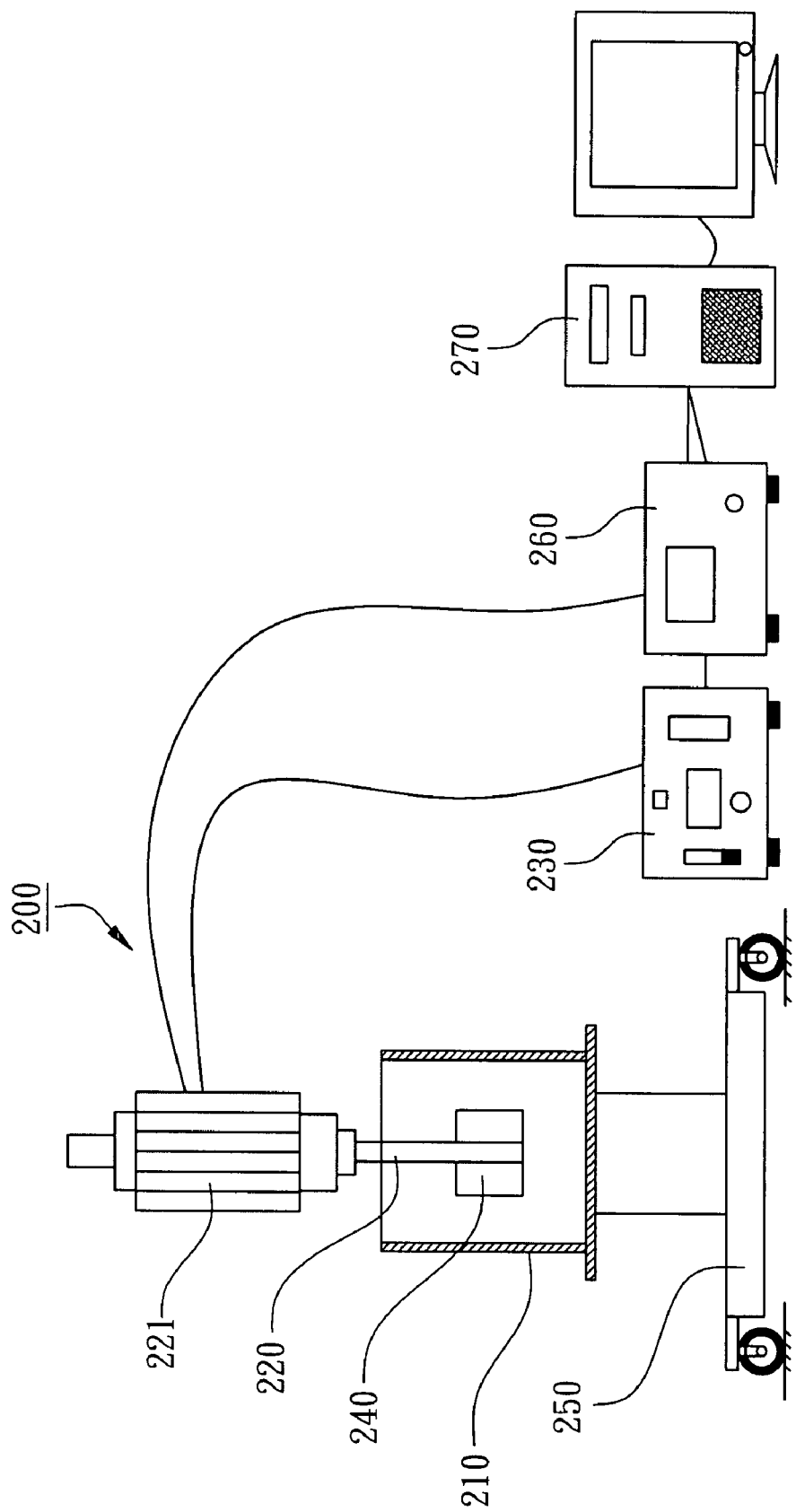
FIG. 6 shows a cross-section of a rheometer according to a first embodiment of the present invention.

Referring to FIGS. 3 and 6, a rheometer 200 of the preferred embodiment of the present invention could determine yield stress and viscosity of cement-based materials. The rheometer 200 includes a drum 210, a rotation shaft 220, a rotational speed controller 230, and an vane-A 240. The drum 210 is used to accommodate cement-based materials, e.g. concrete, mortar or cement paste. One end of the rotation shaft 220 is screwed into foundation 250, and powered by a drive motor 221. The other end of rotation shaft 220 is pushed into the drum 210. The rotational speed controller 230 is used to adjust the rotational speed of rotation shaft 220, such that the rotation shaft 220 could rotate slowly at given speed. In addition, the rheometer 200 further includes a torque display 260 and a data collector 270. The drum 210 is connected to a drum supporting bar 211, and the foundation 250 is fitted with a drum elevating bar 251, which is linked to the drum supporting bar 211 to ensure elevation of drum 210.

Embodiment 2

Figure 7:
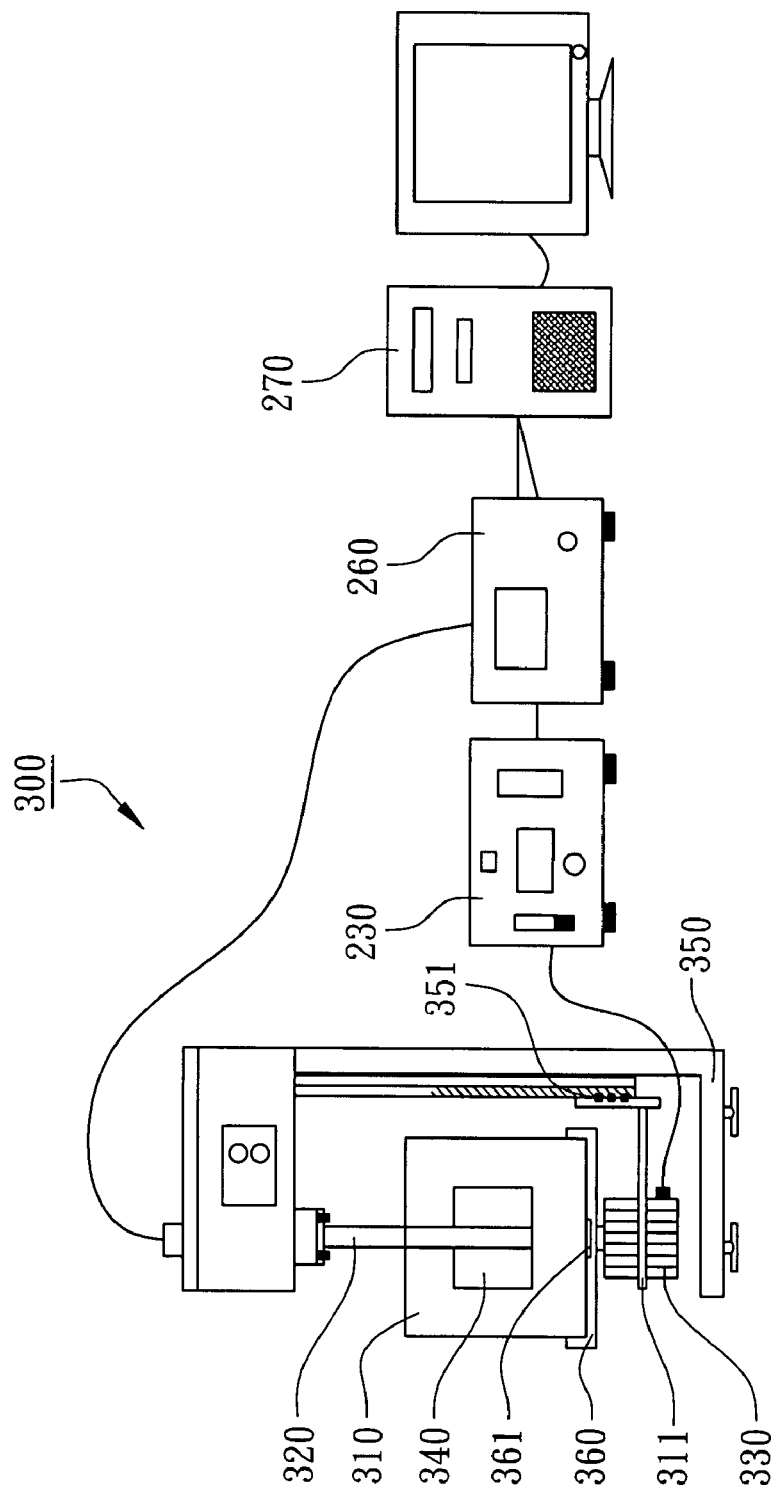
FIG. 7 shows a cross-section of a rheometer according to a second embodiment of the present invention.

Referring to FIG. 7, a rheometer 300, of which the metal shaft 320 is not connected to the motor. Instead, the drive motor 330 is connected to a metal tenon 361 of the drum 310 by a metal disk 360, thus, during testing, the motor 330 drives the drum 310, in turn, driving the concrete and vane-A 240, enabling the measurement of torque of the metal shaft 320.

The rheometer 300 includes a drum 310, a shaft 320, a rotational speed controller 230, and a vane-A 340. The drum 310 is used to accommodate cement-based materials, e.g. concrete, mortar or cement paste and the surface of the drum 310 has serrated surfaces that no slippage occurred. One end of the metallic shaft 320 is screwed into foundation 350, the other end of metallic shaft 320 is pushed into the drum 310, and powered by a drive motor 330. The rotational speed controller 230 is used to adjust the rotational speed of rotation drum 310, such that the rotation drum 310 could rotate slowly at given speed. In addition, the rheometer 300 further includes a torque display 260 and a data collector 270. The drive motor 330 is connected to a supporting bar 311, and the foundation 350 is fitted with an elevating bar 351, which is linked to the supporting bar 311 to ensure elevation of the drive motor 330.

For rheometer 200 and rheometer 300, the vane-A 240, 340 are replaceably connected to a rotation shaft 220 and the metal shaft 320 respectively. And, the vane-A 240 at least has two blades 241. In the preferred embodiment, the blades 241 is a vertical blade (referring to FIG. 8A).

In order to eliminate the jamming from coarse aggregates due to smaller spacing and to reduce the disturbance of concrete arising from rapid rotation of vanes, the ratios of the radius($r_1$) of vane-A 240,340 to the radius($r_0$) of drum 210, drum 310 are preferably set between 0.1~0.6. The gap width ($r_0-r_1$) is at least 2.5 times of maximum aggregate size to prevent the aggregates from being stuck and to avoid the friction from wall of cylinder which may cause an error to the measured torque.

Embodiment 3

Figure 9:
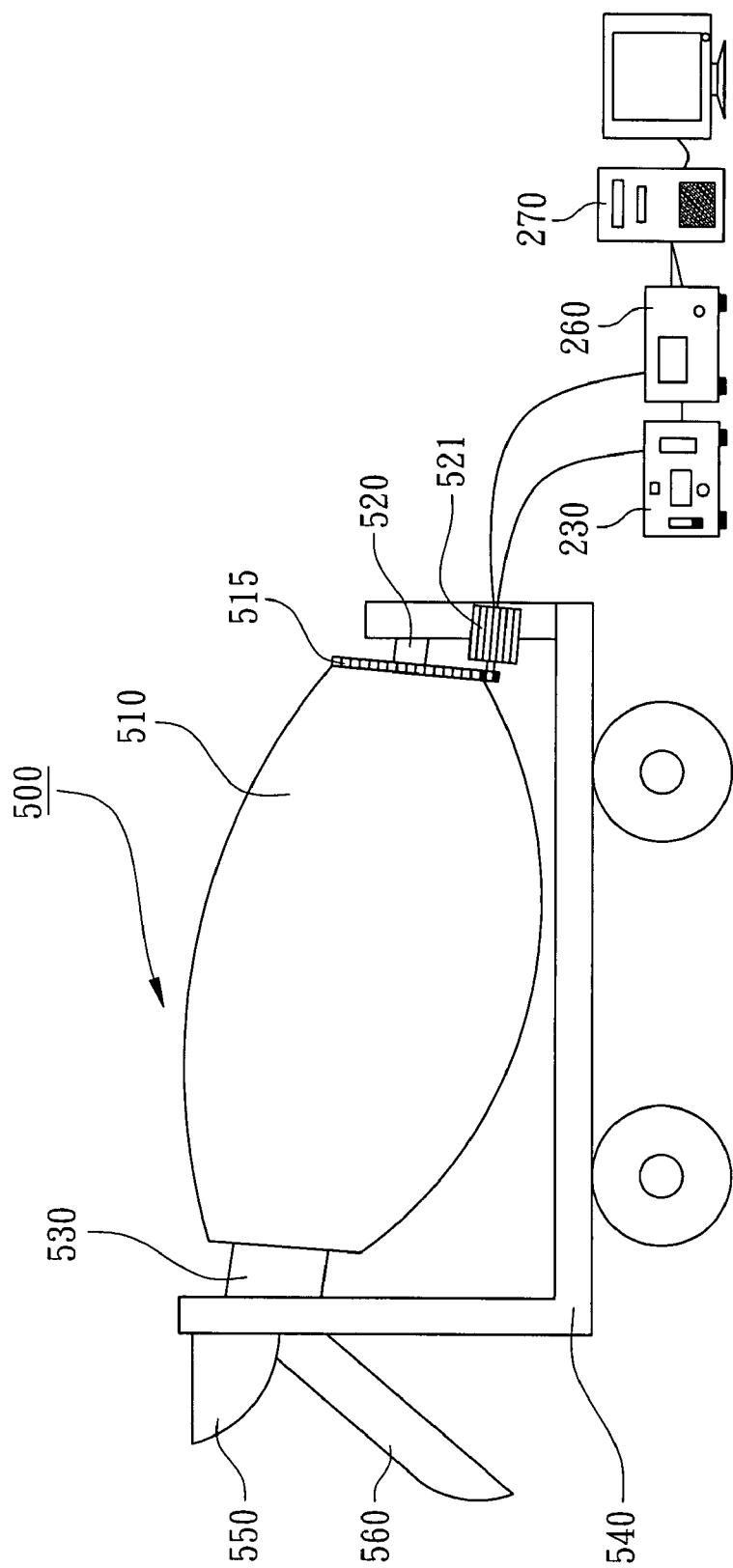
FIG. 9 shows a cross-section of a rheometer according to a third embodiment of the present invention.

Referring to FIG. 9, a preferred embodiment of the present invention, of which a rheometer 500 to measure the rheology of cement-based materials, includes a rotation drum 510, bearings 520, 530, a rotational speed controller 230; the rotation drum 510 can store cement-based materials, such as concrete, mortar, or cement paste, and the inside of the rotation drum 510 has blades to mix the concrete; the rotation drum 510 has a set of gearwheel 515, which is driven by a transmission motor 521; the rotational speed controller 230 can adjust the rotational speed slowly at given speed for the rotation drum 510; the bearing 520 goes through a foundation 540, and the bearing 530 is hollow and goes through a foundation 540, and are connected to inlet 550 and outlet 560; the rheometer 500 can also comprise a torque display 260 and a data collector 270.

Embodiment 4

Figure 10:
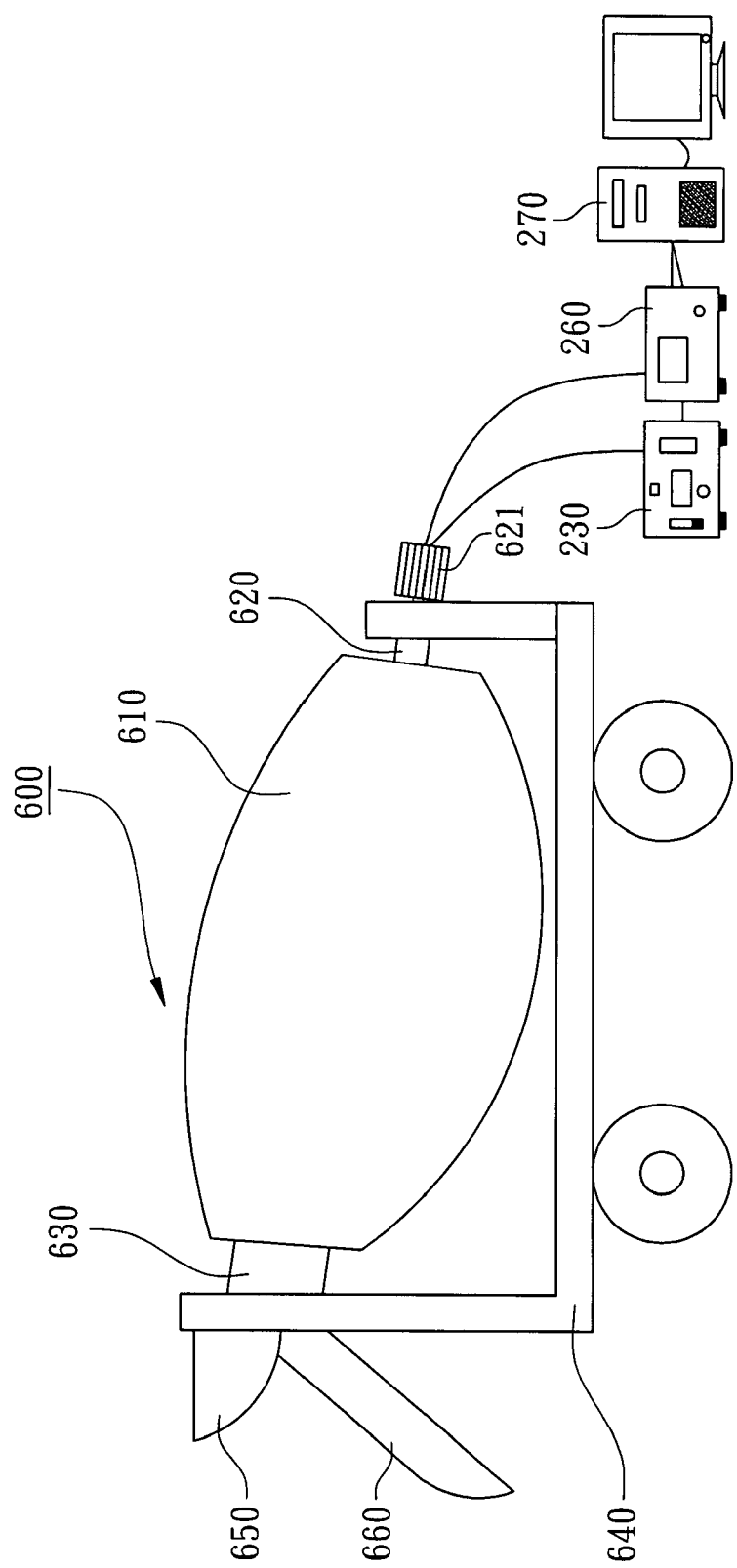
FIG. 10 shows a cross-section of a rheometer according to a fourth embodiment of the present invention.

Referring to FIG. 10, a preferred embodiment of the present invention, of which a rheometer 600 to measure the rheology of cement-based materials, includes a rotation drum 610, bearings 620, 630, a rotational speed controller 230; the rotation drum 610 can store cement-based materials, such as concrete, mortar, or cement paste, and the inside of the rotation drum 610 has blades to mix the concrete; the bearing 620 goes through a foundation 640, and the bearing 630 is hollow and goes through a foundation 640, and are connected to inlet 650 and outlet 660; the rotation drum 610 has a shaft directly geared into a gear of the transmission motor 621, the rotational speed controller 230 can adjust the rotational speed slowly at given speed for the rotation drum 610. The rheometer 600 can also comprise a torque display 260 and a data collector 270.

Experiment (by Invention 1)

In a preferred structure, the drum 210 is designed with a relatively larger diameter, a volume of 108 liter and ratio $r_1/r_0$ 0.36. When the adaptive vane assembly 240 is under stress within concrete due to ration, torque will be measured via rotation shaft 220 and transferred to the torque display 260. Then, Torque (T) and rotational speed (N) are measured and stored in the data acquisition system 270 which is connected to a computer. The measurable range of torque and max. data collection frequency is 0.0001~10 kgf-m and 60/second respectively. Moreover, the rotational speed can be controlled by a computer program or manually. The system can be programmed as constant speed, linear acceleration, quadratic acceleration, and progressive speed change etc. Three sets of adaptive vanes in the preferred embodiment are described below, while the rheology parameters of adaptive vane assembly are listed in Table 1.

Figure 8A:
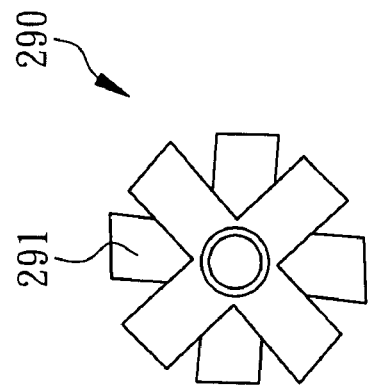
FIG. 8A to 8C are the optimum combination of rheometer vanes.
Figure 8B:
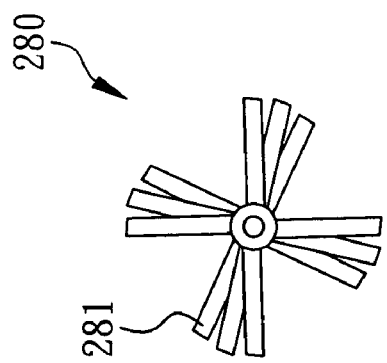
Figure 8C:
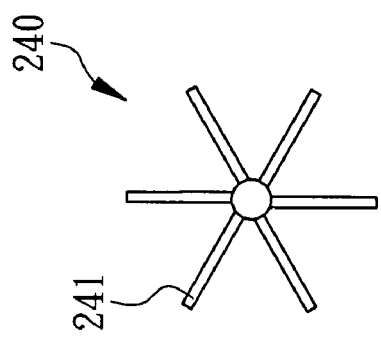

The vane-A 240, vertical six-blades vane with 15 cm in height and 3 mm in thickness is shown FIG. 8A. Three layers vane-B 280, each of which has four blades 281 with the height of 5 cm and a tilted angle of 30°. The phase angle of each layer is: 0°, 22.5°, and 90° (clockwise) as shown FIG. 8B. Three layers vane-C 290, each of which has four blades 291 with the height of 5 cm and a tilted angle of 45°. The phase angle of each layer is: 0°, 22.5°, and 67.5° (counterclockwise) as shown FIG. 8C.

TABLE 1

| Rheological parameter of concrete rheometer | | | |
|---|---|---|---|
| Category of Vanes | G | α | β |
| vane-A 240 | 0.136 | 1 | 917.7 |
| vane-B 280 | 0.115 | Cos30° | 1015.0 |
| vane-C 290 | 0.103 | Cos45° | 1160.7 |

The preferred embodiment of cement-based materials mixed proportions as follow:

Paste

Water to cement ratio (w/c) was 0.37, and the binder was Type☐portland cement. The amount of polycarboxylic acid as admixture was 0.5% of total cement weight.

Mortar w/c was 0.37 and the proportion of weight ratio of water, cement and fine aggregate was 0.37:1.0:3.0. The amount of polycarboxylic acid as admixture was 0.5% of total cement weight.

Concrete

The concrete use in our experiments was available with self-consolidating concrete (SCC), high flowing concrete (HFC) and ordinary Portland concrete (OPC), with their mix proportions shown in Table 2.

Figure 19:
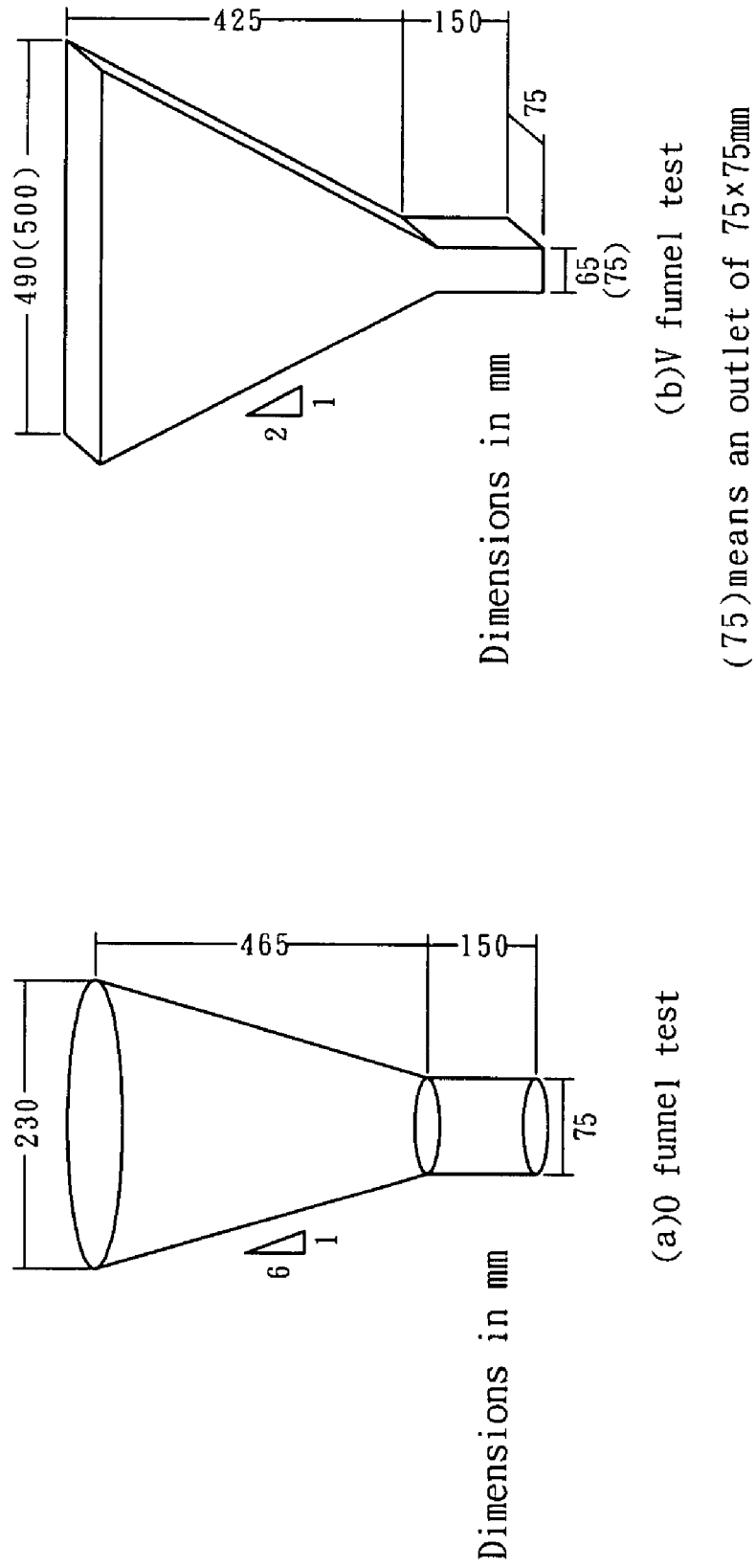
FIG. 19 shows a typical funnel and its dimensions.
Figure 20:
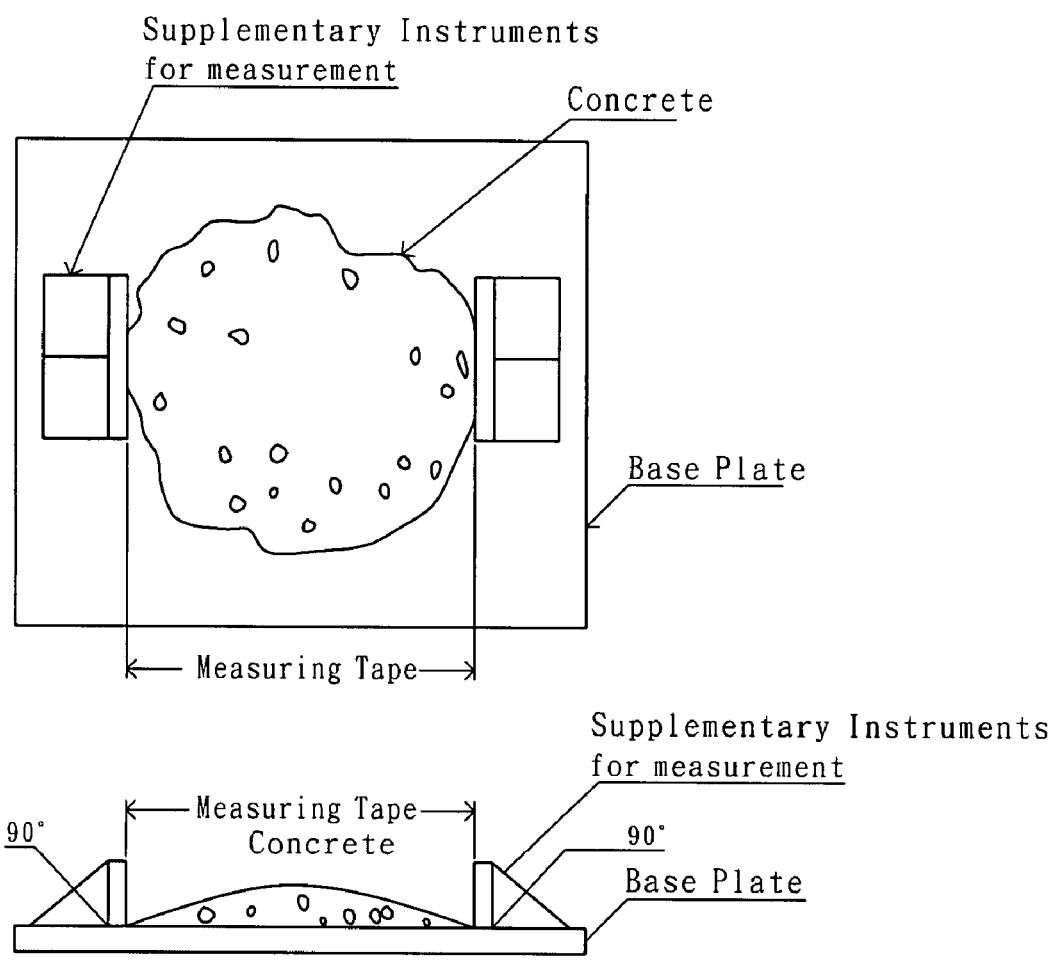
FIG. 20 shows a slump test apparatus for concrete.
Figure 21A:
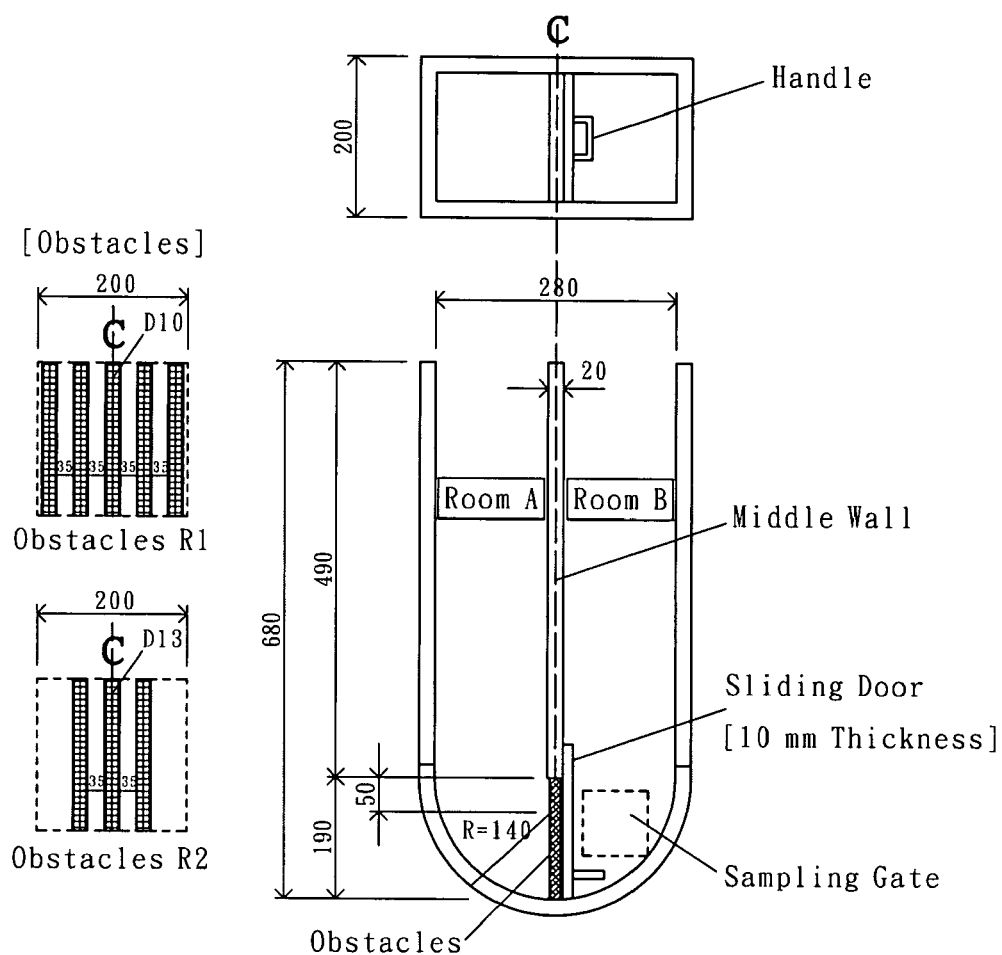
FIGS. 21(*a*) and 21(*b*) are the cross-sections of U-test apparatus.
Figure 21B:
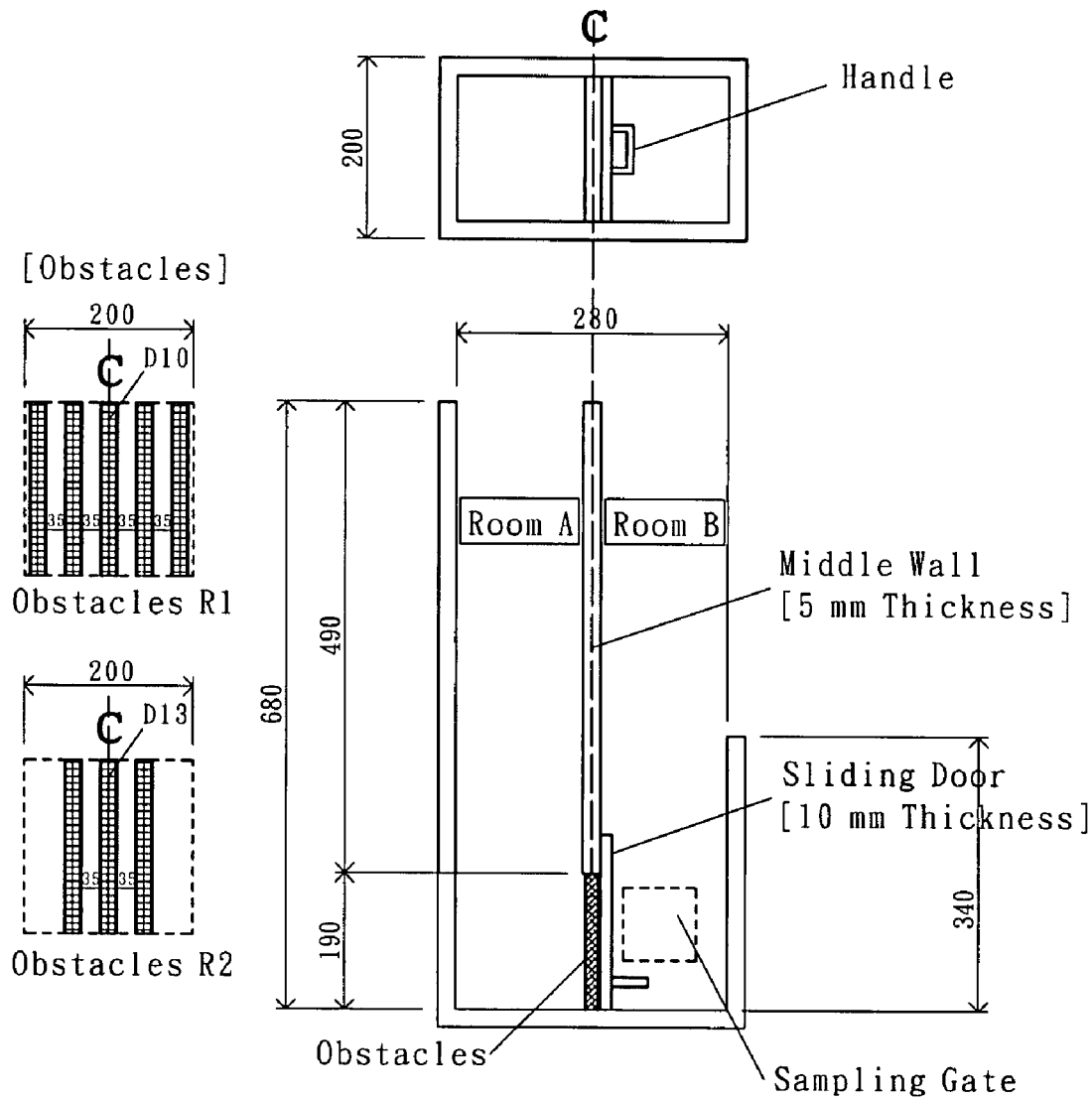
Figure 22:
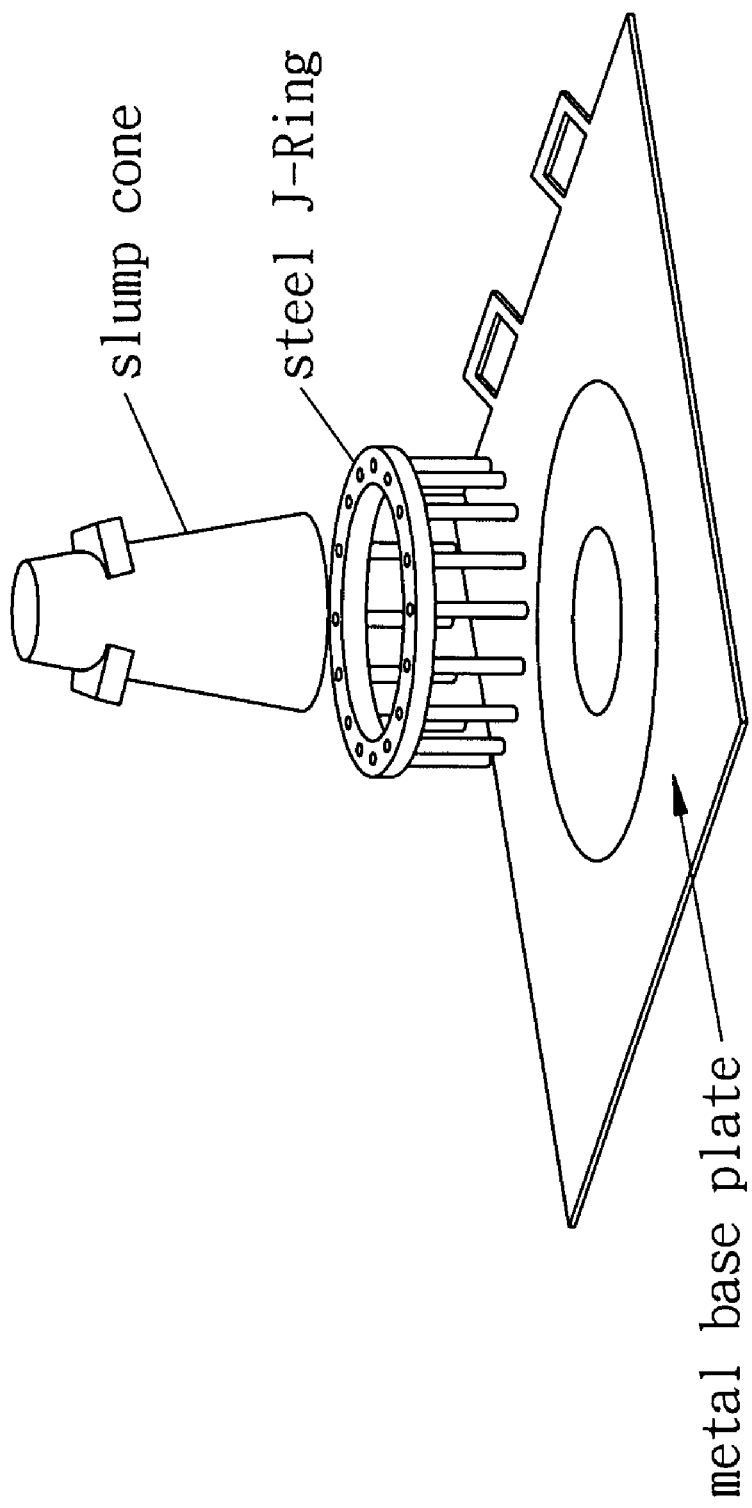
FIG. 22 shows J-Ring test apparatus for concrete.

The mixed proportion design of SCC was verified and passed various tests as shown in FIG. 23, such as V-funnel test (7~20 sec) shown in FIG. 19, slump flow test shown in FIG. 20, U-test (R2, ≧30 cm) shown in FIG. 21(a), 21(b), and J-Ring flow test shown in FIG. 22. With its slump flow between 50~80 cm, HFC is not required to comply with the requirements of SCC but with slump flow above 45 cm. The slump of OPC was 15 cm.

TABLE 2

The concrete mixed proportions

| | | Mix design | | | | | | | |
|---|---|---|---|---|---|---|---|---|---|
| Mixture No. | Concrete type | W/B | Water (Kg/M³) | Cement (Kg/M³) | Slag (Kg/M³) | Fly ash (Kg/M³) | CA (Kg/M³) | FA (Kg/M³) | SP (Kg/M³) | Air (%) |
| 1 | SCC | 0.37 | 185 | 200 | 300 | 0 | 773 | 888 | 5.5 | 2.5 |
| 2 | HPC | 0.40 | 180 | 225 | 180 | 45 | 838 | 867 | 4.8 | 2.5 |
| 3 | OPC | 0.67 | 188 | 280 | 0 | 0 | 1021 | 870 | 2.0 | 1.5 |

The test results of preferred embodiment as follow:

The Rheological Behavior of Cement-Based Materials

Figure 11:
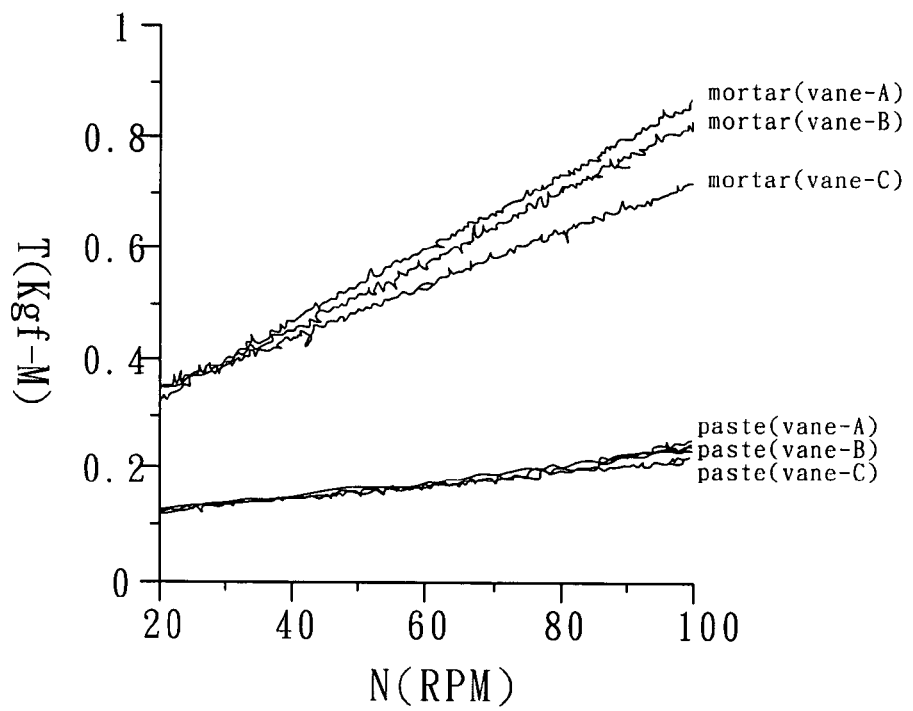
FIG. 11 shows a rheological curve of paste and mortar via concrete rheometer (initial stage).

Because the hydration rate or dispersion state of cement paste structure in this preferred embodiment was changed by addition with the SP, the yield stress and plastic viscosity of the paste were obviously reduced. The flow behavior of cement paste is shown in FIG. 11.

The main difference between mortar and the paste is particle size, which is likely to change the uniformity. Moreover, the larger particle size of mortar increases the friction that makes its rheological behavior well fit the linear model as shown in FIG. 11. Yield stress and plastic viscosity can be used to depict completely the rheological features of mortar.

Figure 12:
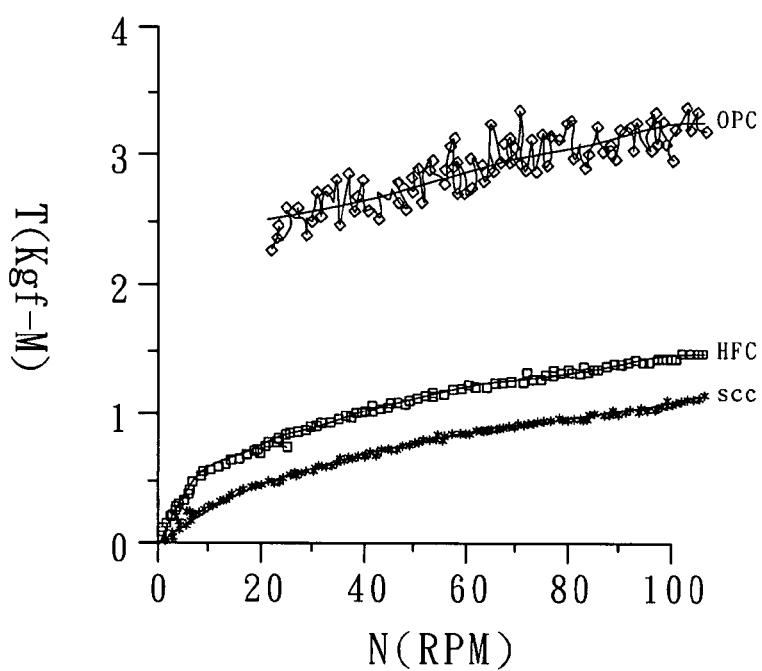
FIG. 12 shows rheological curves of SCC, HFC, OPC via concrete rheometer.

OPC flow behavior can be simulated as linear model when rotation speed is above certain value. A linear regression model can be used for its rheology (only calculated by the value over 20 rpm) as shown in FIG. 12. It showed that the torque values fluctuated erratically because the workability (slump=15 cm) of OPC was low and coarse aggregates caused slippage and percussion during the rotation of vane 240. The flow behavior of OPC fits the linear model.

The rheological behaviors of SCC and HFC are mainly simulated according to the linear regression model. The linear relationship between torque and rotational speed measured by concrete rheometer 200 was shown in Eq. (2). However our experiments demonstrated that the flow behavior of SCC and HFC can also be simulated by the non-linear regression model (FIG. 12). The relationship between the torque and rotational speed is shown in Eq. (8)

$$T = T_0 + aN^b \tag{8}$$

of which: a, b are constants and $T_0$ is y-intercept of the line.

Plastic Viscosity of Cement-Based Materials

Because the rheological behavior of cement paste was analyzed by the non-linear regression model shown in FIG. 11, its plastic viscosity was not a fixed value with the initial state ranged between 5.5~6.6 Pa·s. The rotational speed operated in the experiments was set at 40 rpm. Furthermore, the rheological behaviors of mortar and OPC can also be analyzed as the linear regression model (only calculated by the value over 20 rpm). Take vane-A 240 for example, the plastic viscosity of mortar is 29 Pa·s and OPC is 32 Pa·s.

Figure 13:
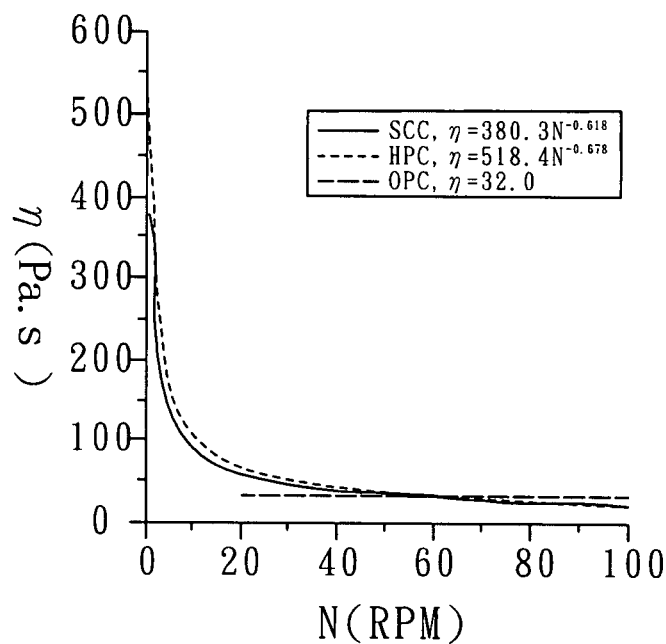
FIG. 13 shows the plastic viscosity curves of SCC, HFC, OPC.

If linear regression model was applied for SCC (e.g. vane-A 240), the plastic viscosity was 32 Pa·s (only calculated by the value over 20 rpm) while the plastic viscosity of SCC in the non-linear regression model was not a fixed value as shown in FIG. 13. The plastic viscosity varied with rotational speed with its initial value was 38.9 Pa·s at rotational speed 40 rpm. The higher the rotational speed, the lower the plastic viscosity. The plastic viscosity of SCC and HFC can be obtained from a power equation as shown in Eq. (9).

$$\eta = q \times N^s \tag{9}$$

Of which:

η=plastic viscosity (Pa·s)

N=rotational speed (rpm)

q, s are constants varied with different materials

Yield Stress of Cement-Based Materials

Figure 14:
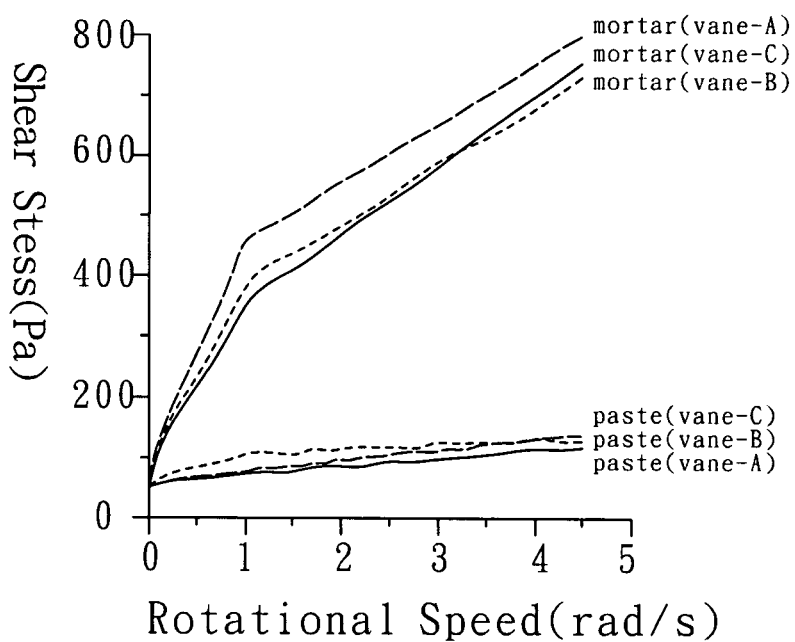
FIG. 14 shows the yield stress curves of paste and mortar via concrete rheometer
Figure 15:
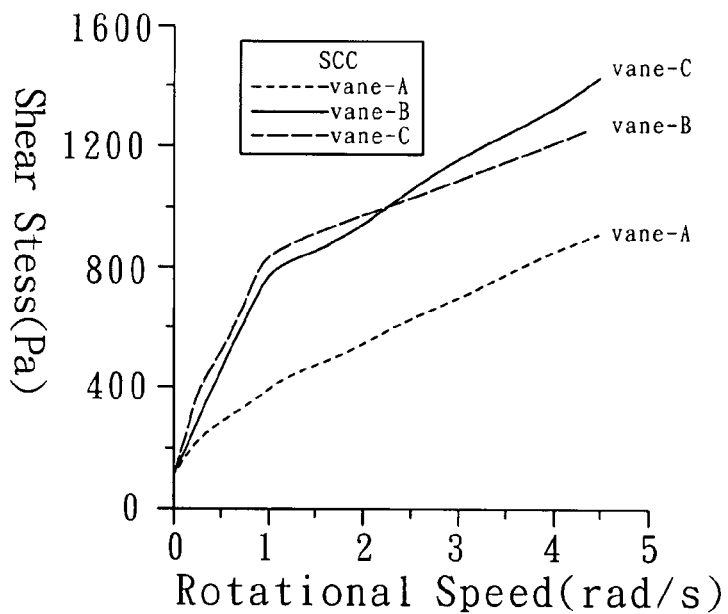
FIG. 15 shows the yield stress curves (initial stage) of SCC via concrete rheometer.
Figure 16:
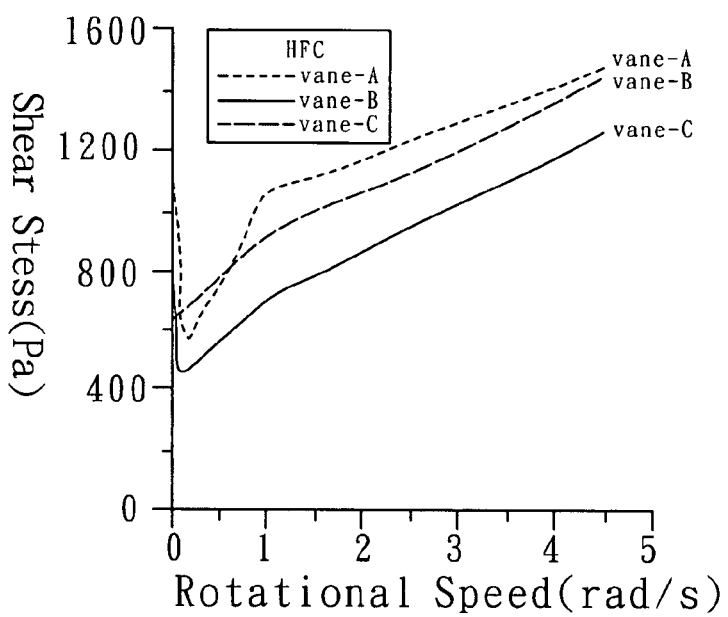
FIG. 16 shows the yield stress curves (initial stage) of HFC via concrete rheometer.

With regard to paste and mortar, the experimental results indicated that yield stress mainly occurred at the rotational speed of 0.01~0.1 (rad/s) as shown in FIG. 14. For HFC and SCC, the experimental results indicated that the yield stress occurred at the rotational speed of 0.01~0.15 (rad/s), with a concave upward curve of the rotational speed and max. shear stress shown in FIG. 15 and FIG. 16.

Figure 17:
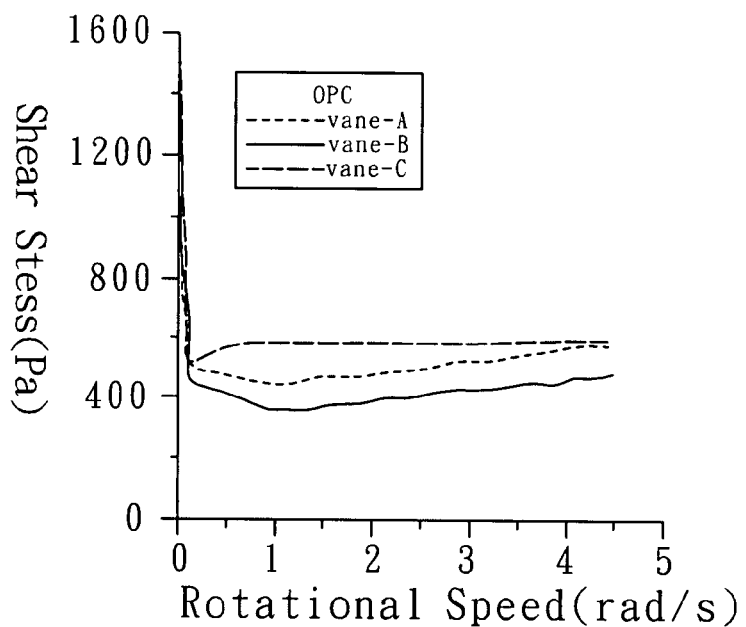
FIG. 17 shows the yield stress curves (initial stage) of OPC via concrete rheometer.

It indicated that OPC had a larger yield stress as shown in the FIG. 17. Because OPC has larger yield stress which results in poor workability, additional compaction and vibration shall be required to reduce the frictional resistance to ensure compactness.

The Effect of Measurement Time on Plastic Viscosity and Yield Stress

Figure 18:
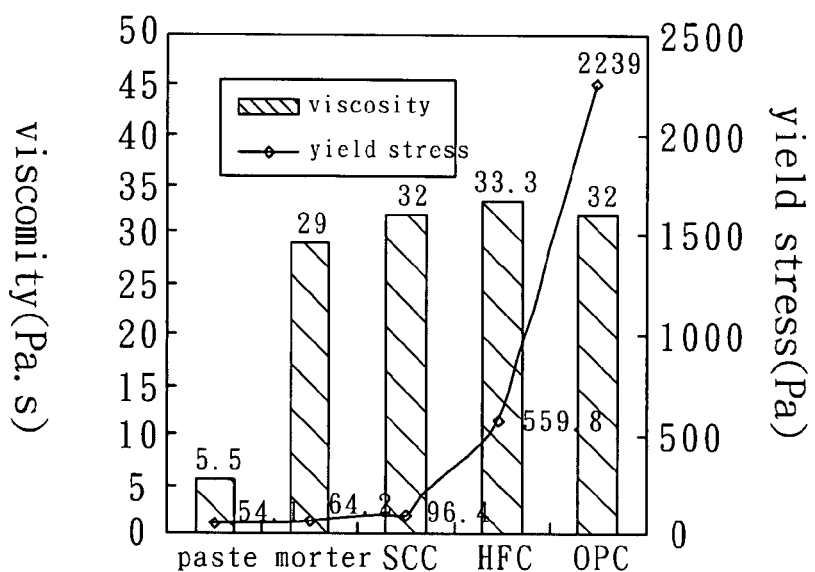
FIG. 18 shows the comparison between plastic viscosity and yield stress of cement-based materials.

FIG. 18 indicates that SCC, HPC, and OPC have a similar value of plastic viscosity but their values of yield stress are remarkably different, of which OPC is 4 times of HFC and 23 times of SCC. Therefore, in order to obtain a concrete with good self-compactability, it is necessary to reduce yield stress and the frictional forces among aggregates. Thus concrete with smaller yield stress will have a better passing ability through reinforcement as shown in Table 3. The passing ability of SCC measured by J-Ring (ASTM C 1621) as shown in Table 4.

TABLE 3

The test results of workability and compressive strength of concrete

| Mixture No. | Concrete type | Slump (cm) | Slump flow (cm) | J-Ring (cm) | U box (cm) | V funnel (sec) | air (%) | $\sigma_7$ (MPa) | $\sigma_{28}$ (MPa) |
|---|---|---|---|---|---|---|---|---|---|
| 1 | SCC | 28/26 | 66/59 | 65/58 | 31/30 | 7/12 | 2.1 | 27.2 | 48.3 |
| 2 | HPC | 27/25 | 65/60 | 55/49 | 26/15 | 8/28 | 1.8 | 23.6 | 39.8 |
| 3 | OPC | 15/9 | — | — | — | — | 1.1 | 15.3 | 22.9 |

$\sigma_7$, $\sigma_{28}$ represents 7-day and 28-day compressive strength, respectively
For the representation of workability test, e.g. slump flow, 66/59 indicates 66 cm is slump flow during initial mixing, and 59 cm is slump flow after 1 hour.

TABLE 4

The passing ability of SCC measured by J-Ring (ASTM C1621).

| Difference in Flows (d1 − d2) | Blocking Assessments |
|---|---|
| 0 to 25 mm (0 to 1 in.) | No Visible Blocking |
| >25 to 50 mm (>1 to 2 in.) | Minimal to Moderate Blocking |
| >50 mm (>2 in.) | Noticeable to Extreme Blocking |

The diameter of the slump flow measurement (d1).
The diameter of the J-Ring flow (d2).

Figure 24:
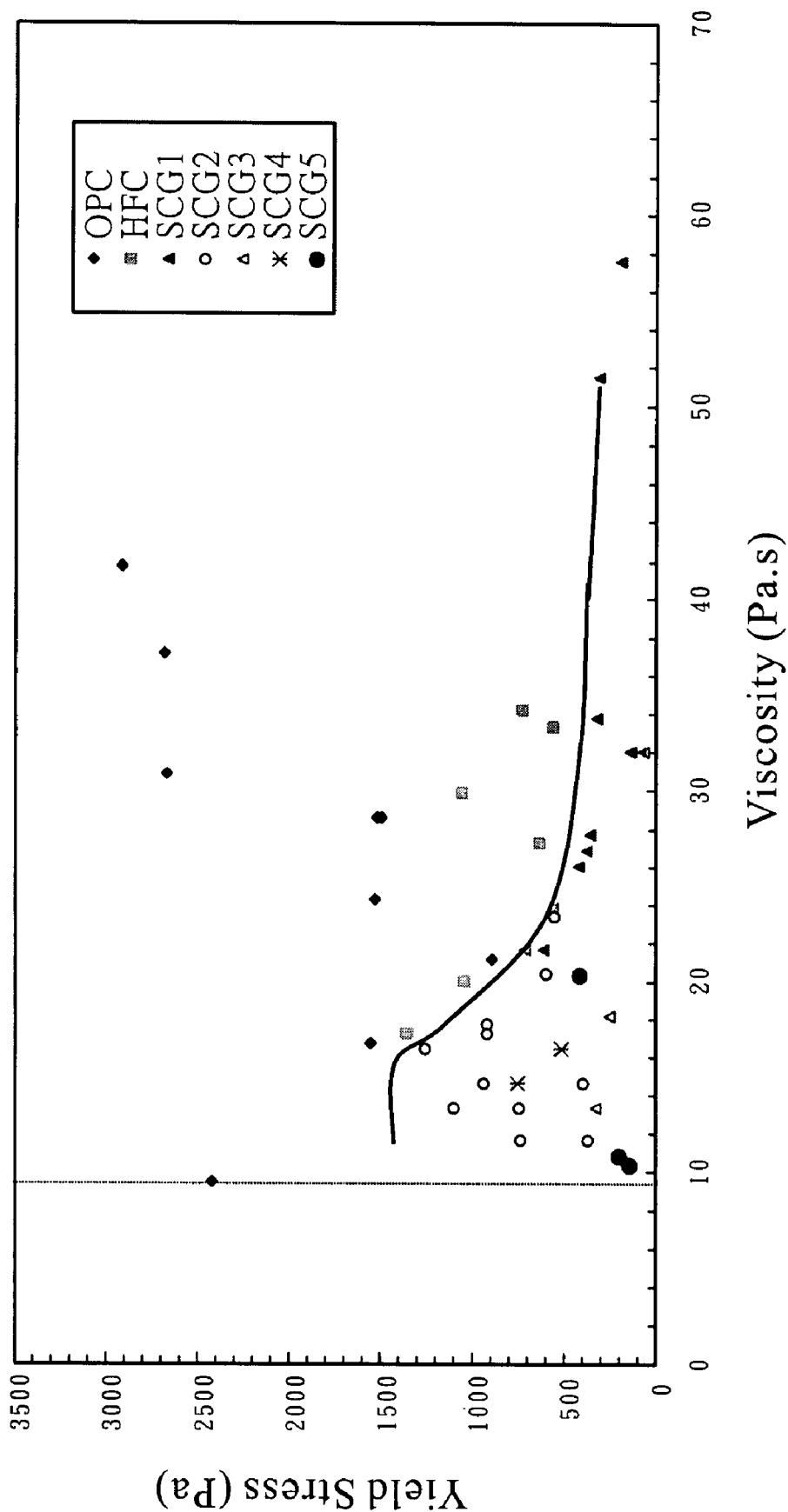
FIG. 24 shows the relationship charts between yield stress and viscosity of OPC, HFC and SCC.
Figure 25:
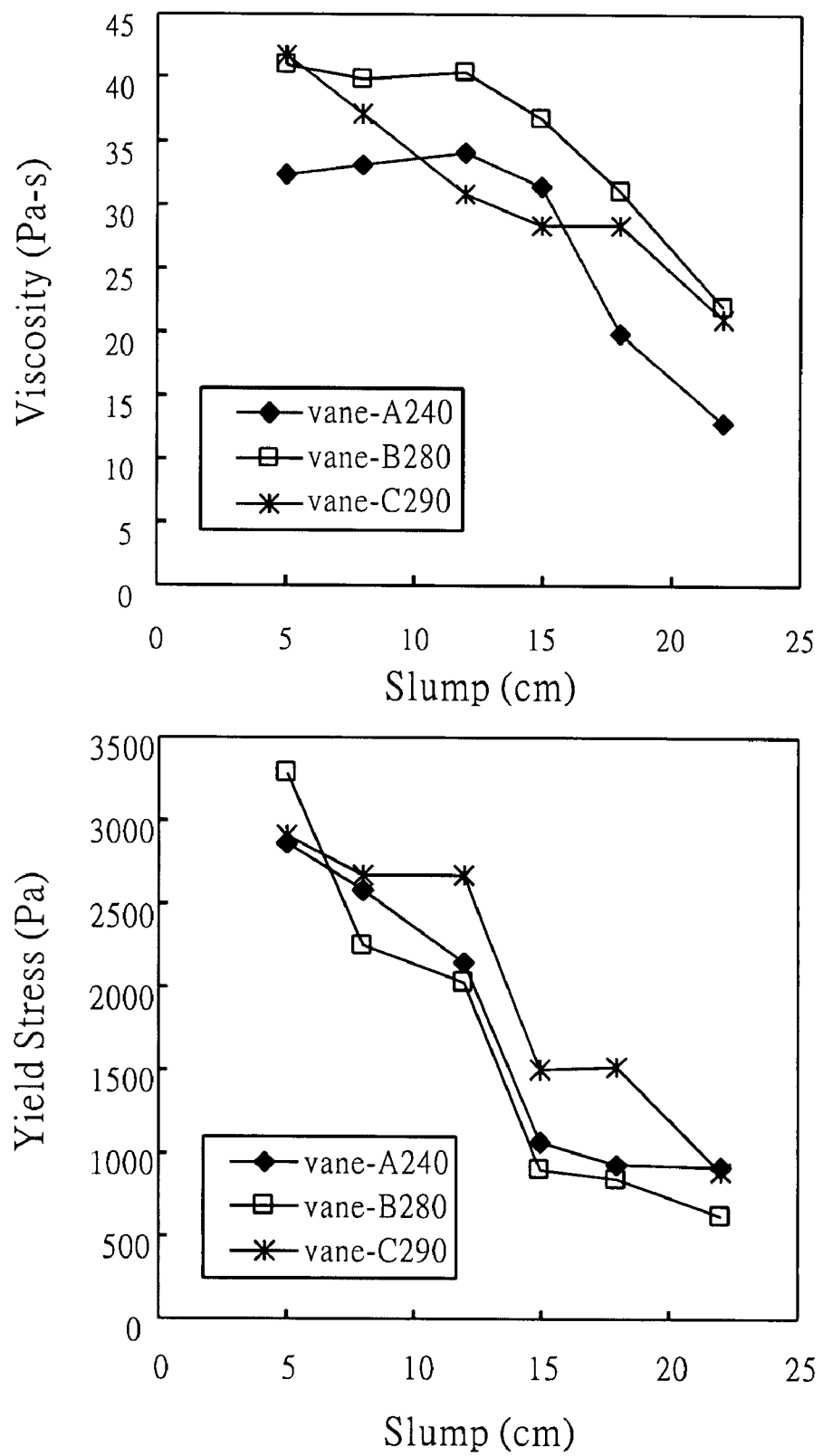
FIG. 25 shows the relationship charts between slump and yield stress/viscosity of OPC.

The range of $\eta$ and $\tau_y$ of SCC, HPC and OPC can be identified using rheometer of the present invention, as illustrated in FIG. 24. Moreover, the concrete slump and corresponding $\eta$ and $\tau_y$ can also be determined as illustrated in FIG. 25. Therefore, the workability of currently available concrete could be judged using the rheometer of present invention, without the use the testers shown in FIGS. 19 to 22, thereby improving the working efficiency and save the labor cost.

Although the invention has been-explained in relation to its preferred embodiment, it is to be understood that many other possible modifications and variations can be made without departing from the spirit and scope of the invention as hereinafter claimed.

What is claimed is:

1. A rheometer (200,300) used to measure rheology of a cement-based material, comprising:
   a drum (210,310) used to accommodate cement-based material;
   a shaft (220,320) having one end pushed into the drum (210,310);
   a rotational speed controller (230) configured to adjust rotational speed of the shaft (220,320) or the drum (210, 310); and
   at least one adaptive vane assembly (240,340,280,290), which is replaceably connected to the shaft (220,320), wherein the adaptive vane assembly (240,340,280,290) contains at least two vanes (241,281,291),
   wherein the ratio ($r_1/r_0$) of radius ($r_1$) of the said adaptive vane assembly (240,340,280,290) to radius ($r_0$) of the drum (210,310) is between 0.1~0.6.

2. The rheometer (200,300) as claimed in claim 1, wherein the gap width ($r_0-r_1$) is at least 2.5 times of maximum aggregate size.

3. The rheometer (200,300) as claimed in claim 1, wherein the vanes (241) of said adaptive vane assembly (240) are vertical vanes.

4. The rheometer (200,300) as claimed in claim 1, wherein the vanes (281,291) of said adaptive vane assembly (280,290) are oblique vanes with included angle in horizontal plane that rotates clockwise or counter-clockwise.

5. The rheometer (200,300) as claimed in claim 1, wherein there are a plurality of said adaptive vane assembly (280,290) mounted onto the shaft (220,320) side-by-side.

6. The rheometer (200,300) as claimed in claim 1, wherein the said cement-based material is selected from the group consisting of concrete, mortar and cement paste.

7. The rheometer (200,300) as claimed in claim 1, wherein the adaptive vane assembly (240,340,280,290) is assembled in a manner to measure viscosity and yield stress of concrete and to determine corresponding slump and slump flow.

8. The rheometer (200,300) as claimed in claim 1, wherein the adaptive vane assembly (240,340,280,290) is assembled in a manner to qualify SCC by measuring torque and rotational speed of concrete.

9. The rheometer (200,300) as claimed in claim 1, wherein the shaft (220) is rotatable.

10. The rheometer (200,300) as claimed in claim 1, wherein the drum (310) is rotatable.

* * * * *